United States Patent

Hisamoto et al.

[11] 4,278,552
[45] Jul. 14, 1981

[54] FLUORINE-CONTAINING BETAINE COMPOUNDS, AND PRODUCTION AND USE THEREOF

[75] Inventors: Iwao Hisamoto; Naonori Enjo, both of Osaka; Chiaki Maeda; Takasige Esaka, both of Kyoto; Yukio Omure; Toshihiko Iida, both of Osaka; Hideki Aomi, Osaka, all of Japan

[73] Assignee: Daikin Kogyo Co., Ltd., Osaka, Japan

[21] Appl. No.: 29,573

[22] Filed: Apr. 12, 1979

[30] Foreign Application Priority Data

Apr. 13, 1978 [JP] Japan .................................. 53-44082

[51] Int. Cl.³ .......................... A62C 1/12; A62D 1/04; C07C 101/24
[52] U.S. Cl. .......................................... 252/3; 169/47; 252/8.05; 252/356; 252/546; 252/DIG. 7; 260/501.13
[58] Field of Search ............ 252/3, 8.05, 546, DIG. 7; 260/501.13; 169/47

[56] References Cited

U.S. PATENT DOCUMENTS

| | | | |
|---|---|---|---|
| 3,258,423 | 6/1966 | Tuve et al. .................................. | 252/3 |
| 3,429,810 | 2/1969 | White ........................................ | 252/3 |
| 3,772,195 | 11/1973 | Francen .................................. | 252/3 X |
| 3,950,417 | 4/1976 | Verdicchio et al. ....... | 252/DIG. 7 X |
| 4,069,158 | 1/1978 | Bertocchio et al. ...................... | 252/3 |
| 4,099,574 | 7/1978 | Cooper et al. ........................ | 252/3 X |
| 4,148,762 | 4/1979 | Koch et al. ........................ | 252/546 X |

Primary Examiner—Richard D. Lovering
Attorney, Agent, or Firm—Birch, Stewart, Kolasch & Birch

[57] ABSTRACT

A fluorine-containing betaine compound of the formula:

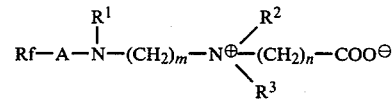

wherein Rf is a polyfluoroalkyl group having 3 to 21 carbon atoms, A is a group of the formula:

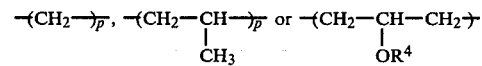

(wherein $R^4$ is a hydrogen atom or an acyl group having 2 or 3 carbon atoms and p is an integer of 1 to 5), $R^1$ is a hydrogen atom, an alkyl group having 1 to 20 carbon atoms or a group of the formula: Rf—A—, $R^2$ and $R^3$ are each a hydrogen atom, an alkyl group having 1 to 3 carbon atoms or a hydroxyalkyl group having 1 to 3 carbon atoms, m is an integer of 2 to 6 and n is an integer of 1 to 4, which is useful as an additive to a foam fire-extinguishing composition for polar organic liquids.

4 Claims, No Drawings

FLUORINE-CONTAINING BETAINE COMPOUNDS, AND PRODUCTION AND USE THEREOF

BACKGROUND OF THE INVENTION

1. Field of the Invention

The present invention relates to fluorine-containing betaine compounds, and production and use thereof. Particularly, it relates to novel fluorine-containing betaine compounds, a process for their preparation and their use as additives for foam fire-extinguishing agents for polar organic liquids.

2. Description of the Prior Art

Conventional foam fire-extinguishing agents for polar organic liquids such as alcohols and ketones are classified into the following two groups: (1) compositions comprising a partially hydrolyzed protein and (2) compositions comprising a synthetic surface active agent. As the composition of the group (1), there is known a composition comprising a partially hydrolyzed protein and, as an additive for improvement of liquid resistance and thermal resistance, a metal salt of a fatty acid dissolved in an aminoalcohol. As the composition of the group (2), there are known a composition (2-1) comprising a foaming surface active agent and, as an additive for the same purpose as in the group (1), a metal salt of a fatty acid dissolved in an aminoalcohol and a composition (2-2) comprising a foaming surface active agent and, as an additive, a water-soluble high polymer such as sodium alginate.

Although these compositions possess a fire-extinguishing ability, each of them has certain drawbacks as mentioned below. In the composition belonging to the group (1), a water-insoluble metal salt of a fatty acid is dispersed in an aqueous solution of a partially hydrolyzed protein so that precipitation is apt to occur during storage for a long time. When the composition is admixed with water at the site of a fire, it must be used within several minutes, because otherwise a precipitate is formed in the water stream which causes a marked decrease of the fire-exinguishing effect. Further, pouring of foams onto the combustive liquid surface should be effected very quietly, or else rapid disappearance of foams is caused to reduce the effect. In some polar organic liquids such as alcohols, ketones, esters and ethers, an insoluble film is formed on the liquid surface and a relatively high effect can be obtained. But in case of amines, aldehydes, carboxylic acids and other similar polar organic liquids, foams are rapidly dissolved in the organic liquid and disappear because of the presence of a metal salt of a fatty acid so that a desirable effect can not be expected.

In compositions belonging to the group (2-1), precipitation during storage or after admixture is hardly caused, but the fire-resistance is insufficient because a synthetic surface active agent is used as the main ingredient, and besides the liquid resistance is inferior in comparison with the group (1). In compositions belonging to the group (2-2), it is expected to cause formation of an air-containing, floating layer in a gel form having a good liquid resistance on the surface of the polar organic liquid by the interaction between the organic liquid and a natural or synthetic high polymer. But, the effect is inferior in comparison with the groups (1) and (2-1). Since the reagent has a high viscosity, a problem is caused in suction and admixture in practical use.

Further, in all of the above mentioned foam fire-extinguishing agents, sea water or standing water is often used at fire-extinguishing, so that precipitation is caused immediately after admixture because of the presence of metal salts contained in sea water or standing water, which results in marked decrease of the fire-extinguishing effect.

On the other hand, aqueous foam compositions comprising water and fluoroalkyl group-containing compounds have been widely employed for fire-exinguishing in oily fire. For example, a foam fire-extinguishing agent comprising derivatives of fluorocarboxylic acid or fluorosulfonic acid is disclosed in Japanese Patent Publication No. 20080/1965. This composition is a foam fire-extinguishing agent usually called "light water" and employed for fire-extinguishing in oily fire. It forms an aqueous film on the oil surface to prevent evaporation of inflammable vapor from the oil surface. Although this fire-extinguishing agent is thus effective for fire-extinguishing in oily fire, an advantageous fire-extinguishing effect cannot be expected in case of fire of polar organic liquids, because an aqueous film is not formed on the liquid surface.

As other type of fire-extinguishing agents for oily fire, there are known protein foam fire-extinguishing agents, of which a typical example is a composition comprising a protein fire-extinguishing compound and a fluorine-containing surface active agent as an additive. For instance, Japanese Patent Publication No. 21078/1972 discloses that, the incorporation of a small amount of a perfluoroalkyl group-containing, water-soluble surface active agent into a hydrolyzed protein is effective in enhancement of the fluidity and fire resistance of fire-extinguishing foams. In fact, all the water-soluble non-ionic or anionic surface active agents having a perfluoroalkyl group as specifically exemplified therein produce an excellent enhancement in oil fire. However, none of them can produce foams of sufficient stability in fire due to polar organic liquids and are practically usable for such fire. Besides, the said patent publication teaches that cationic surface active agents show a tendency to cause precipitation in the fire-extinguishing composition and therefore their use is not desirable.

SUMMARY OF THE INVENTION

For the purpose of improving the stability of fire-extinguishing foams of the fire-extinguishing agent of hydrolyzed protein belonging to the group (1) and also improving the fire resistance of the fire-extinguishing agent of synthetic surface active agent belonging to the group (2) together with enhancing the stability and the fluidity of the fire-extinguishing foams, various fluorine-containing compounds were synthesized, and their effects as additives to those fire-extinguishing agents were examined. As the result, it has now been found that a specific group of novel fluorine-containing betaine compounds are extremely useful as additives for foam fire-extinguishing agents for polar organic liquids. Namely, it has been confirmed that, by incorporation of these compounds into foam fire-extinguishing agents for polar organic liquids, the said problems as mentioned above are solved and an excellent fire-extinguishing ability of polar organic liquids can be obtained.

The main object of the present invention is to provide a fluorine-containing betaine compound represented by the formula:

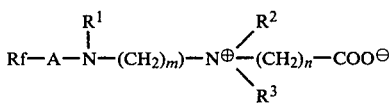

wherein Rf is a polyfloroalkyl group having 3 to 21 carbon atoms, A is a group represented by one of the formulae:

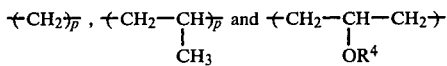

(wherein $R^4$ is a hydrogen atom or an acyl group having 2 or 3 carbon atoms and p is an integer of 1 to 5), $R^1$ is a hydrogen atom, an alkyl group having 1 to 20 carbon atoms or a group of the formula: Rf—A—, $R^2$ and $R^3$ are each a hydrogen atom, an alkyl group having 1 to 3 carbon atoms or hydroxyalkyl group having 1 to 3 carbon atoms, m is an integer of 2 to 6 and n is an integer of 1 to 4.

According to this invention, the fluorine-containing betaine compound (I) can be prepared by reacting a fluorine-containing diamine compound represented by the formula:

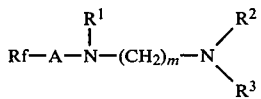

wherein Rf, A, $R^1$, $R^2$, $R^3$ and m are each as defined above with a halogen-substituted alkanoic acid represented by the formula:

X(CH$_2$)$_n$COOH     (III)

wherein X is a halogen atom (except a fluorine atom) and n is as defined above or its salt or an alkanolactone represented by the formula:

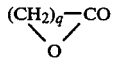

wherein q is an integer of 2 to 4.

In case of using the halogen-substituted alkanoic acid (III) or its salt, the reaction may be carried out, for instance, by heating a mixture or an aqueous solution of an alkali metal salt of the halogen-substituted alkanoic acid (III) with the diamine compound (II) or a mixture of the halogen-substituted alkanoic acid (III) with an alkali metal hydroxide and the diamine compound (II) at 70° to 120° C. for 1 to 5 hours under stirring. After removal of water, the resulting mixture is dissolved into an organic solvent such as ethanol or ether and then cooled. The collected product is, if necessary, recrystallized from suitable solvent so as to enhance the purity.

In case of using the alkanolactone (IV), either one of the diamine compound (II) and the alkanolactone (IV) is dissolved in a suitable solvent and the other is dropwise added thereto under stirring. As the solvent, there may be usually employed a halogenated hydrocarbon (e.g. trichlorotrifluoroethane, methylene chloride), a ketone (e.g. acetone, methyl ethyl ketone), an ether (e.g. diethyl ether), a nitrile (e.g. acetonitrile), etc. These solvents may be used solely or in combination. The optimum reaction temperature is dependent on the kinds of the compounds (II) and (III) as the starting materials. Usually, a temperature from 15° to 80° C. is adopted. The reaction time is usually 1 to 5 hours.

The diamine compound (II) as the starting material is readily obtainable by a conventional procedure. Namely, in case A being —CH$_2$—CH(OH)CH$_2$—, the compound (II) can be obtained by the reaction between the corresponding diamine compound and an epoxide of the formula:

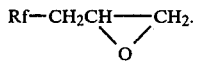

In case of A being —(CH$_2$CH$_2$)$_p$ or

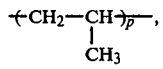

the compound (II) can be prepared by the reaction between the corresponding diamine compound and Rf—CH$_2$CH$_2$)$_p$I or

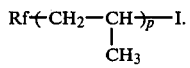

In case of $R^4$ being an acyl group, the compound (II) in which A is —(CH$_2$CH(OH)CH$_2$)— is first obtained by the above mentioned procedure, and then this compound is treated with a carboxylic anhydride to cause acylation.

Specific examples of the fluorine-containing betaine compound (I) thus prepared are shown in Table 1.

TABLE 1

| | | M.P. (°C.) |
|---|---|---|
| (1) | (CF$_3$)$_2$CF(CF$_2$)$_6$CH$_2$CHCH$_2$ with OH, linked to N—(CH$_2$)$_3$—N$^\oplus$(CH$_3$)$_2$—CH$_2$CH$_2$COO$^\ominus$, other N substituent H | 101 |
| (2) | [(CF$_3$)$_2$CF(CF$_2$)$_6$CH$_2$CHCH$_2$-(OH)]$_2$N—(CH$_2$)$_3$—N$^\oplus$(CH$_3$)$_2$—CH$_2$CH$_2$COO$^\ominus$ | 96 |

TABLE 1-continued

| | | M.P. (°C.) |
|---|---|---|
| (3) | $(CF_3)_2CF(CF_2)_6CH_2CH_2$–N(H)–(CH_2)_3–N^⊕(CH_3)_2–CH_2CH_2COO^⊖ | 103 |
| (4) | $[(CF_3)_2CF(CF_2)_6CH_2CH_2]_2$N–(CH_2)_3–N^⊕(CH_3)_2–CH_2CH_2COO^⊖ | 98 |
| (5) | $F(CF_2)_8CH_2CH(OH)CH_2$–N(H)–(CH_2)_2–N^⊕(CH_3)_2–CH_2CH_2COO^⊖ | 93 |
| (6) | $(CF_3)_2CF(CF_2)_6CH_2CH_2$–N(H)–(CH_2)_2–N^⊕(CH_3)_2–CH_2CH_2COO^⊖ | 97 |
| (7) | $F(CF_2)_8CH_2CH_2$–N(H)–(CH_2)_2–N^⊕(C_2H_5)_2–CH_2CH_2COO^⊖ | 95 |
| (8) | $(CF_3)_2CF(CF_2)_6CH_2CH(OH)CH_2$–N(CH_3)–(CH_2)_3–N^⊕(CH_3)_2–CH_2CH_2COO^⊖ | 90 |
| (9) | $(CF_3)_2CF(CF_2)_6CH_2CH(O-C(=O)-CH_3)CH_2$–N(H)–(CH_2)_3–N^⊕(CH_3)_2–CH_2CH_2COO^⊖ | 40 |
| (10) | $[F(CF_2)_8CH_2CH(OH)CH_2]_2$N–(CH_2)_2–N^⊕(CH_3)_2–CH_2COO^⊖ | 107 |

In general, the combustibility or reactivity of polar organic liquids such as alcohols and ketones is dependent upon the polarity, the kinds of functional groups, the number of carbon atoms, etc. Therefore, the fire-extinguishing effect of a fire-extinguishing agent is varied depending on the kind of the polar organic liquid as the object of fire-extinguishing, and none of conventional foam fire-extinguishing agents could produce a sufficient fire-extinguishing effect commonly to various polar organic liquids. By the use of the fluorine-containing betaine compound (I) according to the invention, a satisfactory fire-extinguishing effect can be obtained for a wider range of polar organic liquids such as alcohols, ketones, esters, ethers, aldehydes, carboxylic acids and amines. The fluorine-containing betaine compound (I) has no undesirable influence upon the foaming ability of hydrolyzed proteins and synthetic surface active agents as main ingredients of foam fire-extinguishing agents. When it is incorporated into the organic liquid of fire-extinguishing agent containing such main ingredient, therefore, formation of precipitation is not caused even under storage for a long time, unlike the conventional fire-extinguishing agents, the fire-extinguishing effect being thus maintained.

When, for instance, the fluorine-containing betaine compound (I) is incorporated into a partially hydrolyzed protein, it is used usually in an amount of 0.1 to 30% by weight, preferably 1 to 10% by weight, to the original liquid of a protein foaming agent (3%-type or 6%-type). Into the resultant mixture, other additives such as a surface active agent and a freezing-preventing agent may be further incorporated in case of necessity. The thus obtained composition is usually diluted with water and employed according to the conventional techniques.

In case of the foaming agent being a synthetic surface active agent such as sodium lauryl sulfate, the fluorine-containing betaine compound (I) may be used almost in the same proportion to the original liquid of the foaming agent as above to afford a composition useful as a foam fire-extinguishing agent for polar organic liquids.

The fluorine-containing betaine compound (I) is very useful as an additive not only for the said foam fire-extinguishing agents for polar organic liquids but also for foam fire-extinguishing agents for oily fire. Owing to its specific surface activity, the betaine compound (I) is further utilizable for various uses such as additives for cleaners, waxes, haze-preventing agents and various etching agents and evaporation-inhibiting agents.

The present invention will be hereinafter explained further in detail in the following Examples and Comparative Examples.

EXAMPLE 1

Preparation of (1):

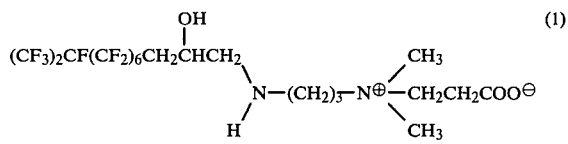

(A) In a 350 ml-volume three-necked flask equipped with a reflux condenser, a stirring apparatus and a dropping funnel, ethanol (150 ml) and N,N-dimethylaminopropylamine (102 g, 1.0 mol) were charged, and while stirring at 60° C. in a water bath kept at 60° C., an epoxide compound represented by the formula:

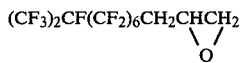

was added dropwise thereto through the dropping funnel. After the addition of this epoxide (52.6 g, 0.10 mol) in 90 minutes, stirring was continued for an additional 90 minutes under heating. The reaction mixture was subjected to gas chromatographic analysis under temperature-elevation (column, Silicone SE-30, 3 m; column temperature, temperature-elevation of 100° C.–4° C./min), whereby it was confirmed that the starting epoxide was completely consumed, and a peak of the known substance of the formula: $(CF_3)_2CF(CF_2)_6$—CH=CH—CH$_2$OH was observed, in addition to the objective compound as the main product.

The whole reaction mixture was poured into an evaporater, and the unreacted amine and the said by-product were eliminated at 120° C. under a pressure of 10 mmHg to obtain a product with a gas chromatographic purity of 97% (61 g). The thus obtained main product was subjected to a GC-MS analysis, and from the obtained data, which are shown below, this product was proved to be the compound of the formula:

$$\underset{H}{(CF_3)_2CF(CF_2)_6CH_2\overset{OH}{\underset{|}{C}}HCH_2}\diagdown N-(CH_2)_3-N\diagup\overset{CH_3}{\underset{CH_3}{}}\tag{1a}$$

Apparatus:
Shimadzu LKB-9000 type
Conditions:
Gas-Chro column SE-30, 3 m
column temperature, elevated with a rate of 4° C./min from 100° C.
ionization voltage, 70 eV

| Main peaks (m/e): | Ion |
|---|---|
| 629 | (M + H)$^+$ (M = mother ion) |
| 590 | (M − 2F)$^+$ |
| 556 | Rf—CH$_2$CH(OH)CH$_2$NHCH$_2$$^+$ |
| Main peaks (m/e): | Ion |
| 58 | (CH$_3$)$_2$NCH$_2$$^+$ |
| 85 | (CH$_3$)$_2$NC$_3$H$_5$$^+$ |

(B) In a 300 ml-volume three-necked flask equipped with a reflux condenser, a stirring apparatus and a dropping funnel, a mixture of trichlorotrifluoroethane and acetonitrile (50/50 by volume) (100 ml) and β-propiolactone (3.2 g, 0.044 mol) were charged, and while stirring at 30° C. in a water bath, the compound (1a) which was diluted 6 times by weight with the said solvent mixture of trichlorotrifluoroethane/acetonitrile was dropwise added thereto. After the addition of this compound (25.1 g, 0.04 mol) in 120 minutes, stirring was continued for further 90 minutes. After the reaction, the solid precipitate was collected by filtration, washed well with a solvent mixture of trichlorotrifluoroethane/acetonitrile (50/50 by volume) and dried in vacuum to obtain a product (18 g).

By the conventional bromophenol blue test and methylene blue test, this product was confirmed to possess a property as a betaine type amphoteric active agent.

In the IR absorption spectrum, the strong absorption at 1830 cm$^{-1}$ which was seen in the starting β-propiolactone and derived from stretching vibration of >C=O disappeared, and strong absorptions at 1590 cm$^{-1}$ (—COO$^-$) and at 1100–1300 cm$^{-1}$ (—CF) and other absorptions were observed.

The result of the elementary analysis corresponded well to the theoretical values as shown below:

| | Found | Calcd. |
|---|---|---|
| C | 34.1 (%) | 34.3 (%) |
| H | 3.2 | 3.3 |
| F | 51.2 | 51.6 |
| N | 4.1 | 4.0 |
| O | (7.4)* | 6.8 |
| Sum | 100.0 | 100.0 |

Note:
*Value obtained by substracting the sum of C, H, F and N from 100.

EXAMPLE 2

Preparation of (3):

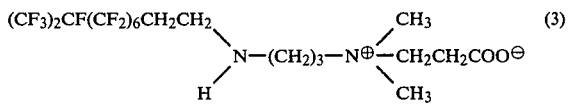

(A) In a 100 ml-volume three-necked flask equipped with a reflux condenser, a stirring apparatus and thermometer, an iodine compound of the formula: (CF$_3$)$_2$CF(CF$_2$)$_6$CH$_2$CH$_2$I (18.7 g, 0.03 mol) and N,N-dimethylaminopropylamine (30.6 g, 0.3 mol) were charged, and the contents were stirred for 4 hours in a water bath kept at 90° C. By the gas chromatographic analysis, it was confirmed that the starting iodine compound was consumed by the reaction almost completely.

After the reaction, the reaction mixture was poured into a separating funnel and washed well with a 2% by weight NaOH solution and then with water several times. The washed mixture was then poured into an evaporater, and the unreacted amine and other substances were eliminated at 120° C. under a pressure of 10 mmHg to obtain a product with a gas chromatographic purity of 97.5% (10.5 g).

From the data obtained by the GC-MS analysis under the same condition as in Example 1, the product was proved to be the compound of the formula:

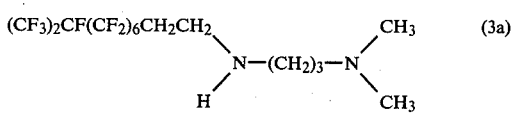

| Main peaks (m/e): | Ion |
|---|---|
| 579 | $(M - F)^+$ ($M$ = mother ion) |
| 558 | $(M - 2HF)^+$ |
| 101 | $(CH_3)_2NCH_2CH_2CH_2NH^+$ |

(B) In a 100 ml-volume three-necked flask equipped with a reflux condenser, a stirring apparatus and a dropping funnel, the compound (3a) obtained in (A) (9.0 g, 0.015 mol) and acetone (50 ml) were charged, and while stirring at 30° C. in a water bath, β-propiolactone which was diluted 5 times by weight with acetone was dropwise added thereto. After the addition of β-propiolactone (1.45 g, 0.02 mol) in 30 minutes, stirring was continued for further 60 minutes. By gas chromatographic analysis, it was confirmed that the starting material (3a) was consumed by the reaction almost completely.

After the reaction, the reaction mixture was poured into an evaporater to eliminate acetone and the residue was purified by recrystallization from a solvent mixture of ethanol/n-hexane (30/70 by volume). The solid product isolated from the solvent was dried in vacuum to obtain a product (5.0 g). By the bromophenol blue test and methylene blue test as in Example 1, this product was confirmed to possess a property as a betaine type amphoteric active agent. In the IR absorption spectrum, the strong absorption at 1830 cm$^{-1}$ (>C=O) seen in -propiolactone disappeared, and strong absorptions at 1590 cm$^{-1}$ (—COO−) and at 100-1300 cm$^{-1}$ (—CF) and other absorptions were observed.

The result of the elementary analysis corresponded well to the theoretical values as shown below:

|   | Found | Calcd. |
|---|---|---|
| C | 33.8 (%) | 34.0 (%) |
| H | 3.2 | 3.1 |
| F | 53.4 | 53.9 |
| N | 4.3 | 4.2 |
| O | (5.3)* | 4.8 |
| Sum | 100.0 | 100.0 |

Note:
*Value obtained by substracting the sum of C, H, F and N from 100.

EXAMPLE 3

A foam fire-extinguishing composition was prepared from the following components:

|   | Part(s) (by weight) |
|---|---|
| Protein foam fire-extinguishing agent of 3% type (comprising hydrolyzed protein and additives such as iron salts) | 3.0 |
| Surface active agent (the fluorine-containing betaine compound (1) shown in Table 1) | 0.1 |
| Water | 96.9 |

This composition (100 ml) was charged into a 1 liter volume polyethylene vessel and the contents were stirred for 2 minutes under a speed of 2,000 rpm by the aid of a stirring wing inserted into the vessel to prepare foam. The volume of the produced foam was read from the volume graduations on the vessel. The foam (20 ml) was taken out and placed on the surface of methanol or acetone (70 ml) contained in a 100 ml volume beaker, and measurement of time by a stop watch was started.

The amounts of remaining foam after 10 and 20 minutes were determined by macroscopic measurement. The results are shown in Table 3.

EXAMPLES 4 to 7

A foam fire-extinguishing composition was prepared from the same components as in Example 3 but using as the surface active agent the fluorine-containing betaine compound (3), (2) or (7) shown in Table 1 or the compound of the formula:

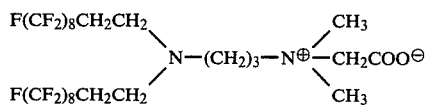

The same test for foam stability was carried out. The results are shown in Table 3.

Comparative Examples 1 to 10

A foam fire-extinguishing composition was prepared from the same components as in Example 3 but using no surface active agent or using a conventional fluorine-containing surface active agent shown in Table 2, and the same test for foam stability was carried out. The results are shown in Table 3.

TABLE 2

| Comparative Example No. | Surface active agent |
|---|---|
| 1 | Not used |
| 2 | $F(CF_2)_8SO_2-\underset{\underset{C_3H_7}{\mid}}{N}-CH_2COOK$ |
| 3 | $F(CF_2)_7COONH_4$ |
| 4 | $F(CF_2)_8OC_6H_4SO_3K$ |
| 5 | $F(CF_2)_8SO_2-\underset{\underset{C_3H_7}{\mid}}{N}-(CH_2CH_2O)_{10}H$ |
| 6 | $F(CF_2)_8SO_2-\underset{\underset{C_3H_7}{\mid}}{N}-(CH_2CH_2O)_{10}SO_3K$ |
| 7 | 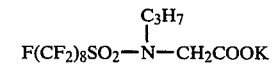 |
| 8 | 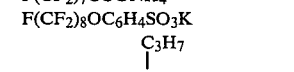 |
| 9 | 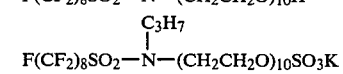 |
| 10 | 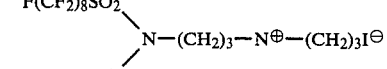 |

TABLE 3

| Kind of foam fire-extinguishing agent | Multiplication of foaming* | Polar solvent | Stability of foam After 10 minutes | After 20 minutes |
|---|---|---|---|---|
| Example 3 | 9 | Acetone | 90% remaining | 70% remaining |
|  |  | Methanol | 90% remaining | 80% remaining |
| Example 4 | 9 | Acetone | 80% remaining | 60% remaining |
|  |  | Methanol | 80% remaining | 70% remaining |
| Example 5 | 9 | Acetone | 90% remaining | 70% remaining |
|  |  | Methanol | 90% remaining | 70% remaining |
| Example 6 | 8 | Acetone | 80% remaining | 50% remaining |
|  |  | Methanol | 80% remaining | 60% remaining |
| Example 7 | 8 | Acetone | 90% remaining | 70% remaining |
|  |  | Methanol | 90% remaining | 70% remaining |
| Comparative Example 1 | 9 | Acetone | Disappearing within 5 seconds | — |
|  |  | Methanol |  |  |
| Comparative Example 2 | 8 | Acetone | Disappearing within 10–12 seconds | — |
|  |  | Methanol |  |  |
| Comparative Example 3 | 9 | Acetone | Disappearing within 5–7 seconds | — |
|  |  | Methanol |  |  |
| Comparative Example 4 | 3 | Acetone | Disappearing within 5 seconds | — |
|  |  | Methanol |  |  |
| Comparative Example 5 | 3 | Acetone | Disappearing within 5 seconds | — |
|  |  | Methanol |  |  |
| Comparative Example 6 | 3 | Acetone | Disappearing within 5 seconds | — |
|  |  | Methanol |  |  |
| Comparative Example 7 | 8 | Acetone | Disappearing within 5–7 seconds | — |
|  |  | Methanol |  |  |
| Comparative Example 8 | 9 | Acetone | 10% remaining | 5% remaining |
|  |  | Methanol | 20% remaining | 10% remaining |
| Comparative Example 9 | 9 | Acetone | 20% remaining | 10% remaining |
|  |  | Methanol | 20% remaining | 10% remaining |
| Comparative Example 10 | 8 | Acetone | remaining | remaining |
|  |  | Methanol | Disappearing within 5–7 seconds | — |

Note:
*Multiplication of foaming = volume of foam (ml)/100 (ml)

EXAMPLE 8

Using the compositions prepared in Example 3, Example 6, Comparative Example 1, Comparative Example 2 and Comparative Example 7, the following test was carried out.

Into a B fire model (0.45 m×0.45 m×0.3 m; 0.2 m²), methanol (20 liters; height of liquid surface, 20 cm) was poured, and the model was ignited. After 5 minutes, the said composition was continuously ejected through a foaming nozzle (1 lit/min/5 kg/cm²) for 5 minutes to produce foam. Measurement of time was started simultaneously with the initiation of the ejection, and the time required for inhibition of fire by the foam spreading on the combustive surface of methanol and the time required for complete fire-extinguishing were recorded as the combustion-inhibiting time and the fire-extinguishing time, respectively. After completion of the continuous foaming for 5 minutes, the model was allowed to stand still for 15 minutes. Then, flame of a torch stick was made to come near the liquid surface to effect recombustion test (torch test). The results are shown in Table 4.

The same test was repeated as above but using another foaming nozzle (0.5 lit/min/5 kg/cm²). The results are shown in Table 5.

TABLE 4

| | Composition | | | | |
|---|---|---|---|---|---|
| | Example 3 | Example 6 | Comparative Example 1 | Comparative Example 2 | Comparative Example 7 |
| Inhibiting time | 40 sec. | 50 sec. | not inhibited | not inhibited | 1 min. and 50 sec. |
| Fire-extinguishing time | 1 min. | 1 min. and 20 sec. | not extinguished | not extinguished | 2 min. and 20 sec. |
| Torch test | not ignited | not ignited | not determined | not determined | not ignited |

TABLE 5

| | Composition | | | | |
|---|---|---|---|---|---|
| | Example 3 | Example 6 | Comparative Example 1 | Comparative Example 2 | Comparative Example 7 |
| Inhibiting time | 2 min. | 2 min. and 10 sec. | not inhibited | not inhibited | not inhibited |
| Fire-extinguishing time | 2 min. and 40 sec. | 3 min. and 10 sec. | not extinguished | not extinguished | not extinguished |
| Torch test | not ignited | not ignited | not determined | not determined | not determined |

We claim:
1. A fluorine-containing betaine compound of the formula:

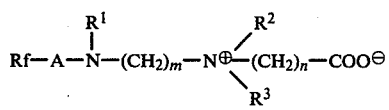

wherein Rf is polyfluoroalkyl group having 3 to 21 carbon atoms, A is a group of the formula:

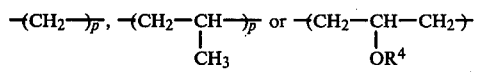

(wherein $R^4$ is a hydrogen atom or an acyl group having 2 or 3 carbon atoms and p is an integer of 1 to 5), $R^1$ is a hydrogen atom, an alkyl group having 1 to 20 carbon atoms or a group of the formula: Rf—A—, $R^2$ and $R^3$ are each a hydrogen atom, an alkyl group having 1 to 3 carbon atoms or a hydroxyalkyl group having 1 to 3 carbon atoms, m is an integer of 2 to 6 and n is an integer of 1 to 4.

2. A process for preparing fluorine-containing betaine compounds which comprises reacting a fluorine-containing diamine compound of the formula:

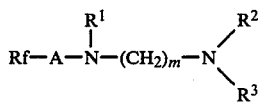

wherein Rf is a polyfluoroalkyl group having 3 to 21 carbon atoms, A is a group of the formula:

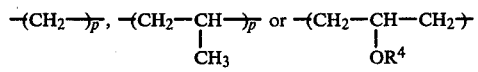

(wherein $R^4$ is a hydrogen atom or an acyl group having 2 or 3 carbon atoms and p is an integer of 1 to 5), $R^1$ is a hydrogen atom, an alkyl group having 1 to 20 carbon atoms or a group of the formula: Rf—A—, $R^2$ and $R^3$ are each a hydrogen atom, an alkyl group having 1 to 3 carbon atoms or a hydroxyalkyl group having 1 to 3 carbon atoms and m is an integer of 2 to 6 with a halogen-substituted alkanoic acid having 2 to 5 carbon atoms or its salt or an alkanolactone having 3 to 5 carbon atoms to obtain a fluorine-containing betaine compound of the formula:

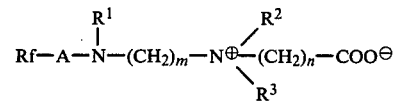

wherein Rf, A, $R^1$, $R^2$, $R^3$ and m are each as defined above and n is an integer of 1 to 4.

3. An additive to a foam fire-extinguishing agent for polar organic liquids which comprises a fluorine-containing betaine compound of the formula:

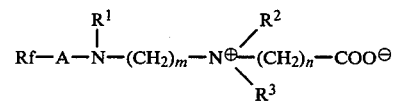

wherein Rf is a polyfluoroalkyl group having 3 to 21 carbon atoms, A is a group of the formula:

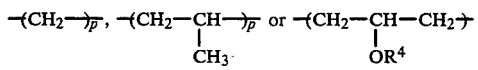

(wherein $R^4$ is a hydrogen atom or an acyl group having 2 to 3 carbon atoms and p is an integer of 1 to 5), $R^1$ is a hydrogen atom, an alkyl group having 1 to 20 carbon atoms or a group of the formula: Rf—A—, $R^2$ and $R^3$ are each a hydrogen atom, an alkyl group having 1 to 3 carbon atoms or a hydroxyalkyl group having 1 to 3 carbon atoms, m is an integer of 2 to 6 and n is an integer of 1 to 4.

4. A foam fire-extinguishing composition for polar organic liquids which comprises an aqueous solution of a partially hydrolyzed protein and, as an additive contained therein, 0.1 to 30% by weight based on the original liquid of the protein solution of a fluorine-containing betaine compound of the formula:

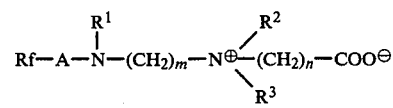

wherein Rf is a polyfluoroalkyl group having 3 to 21 carbon atoms, A is a group of the formula:

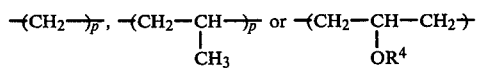

(wherein $R^4$ is a hydrogen atom or an acyl group having 2 or 3 carbon atoms and p is an integer of 1 to 5), $R^1$ is a hydrogen atom, an alkyl group having 1 to 20 carbon atoms or a group of the formula: Rf—A—, $R^2$ and $R^3$ are each a hydrogen atom, an alkyl group having 1 to 3 carbon atoms or a hydroxyalkyl group having 1 to 3 carbon atoms, m is an integer of 2 to 6 and n is an integer of 1 to 4.

* * * * *